United States Patent [19]

DeLuca et al.

[11] Patent Number: 4,564,474

[45] Date of Patent: * Jan. 14, 1986

[54] 23,23-DIFLUORO-25-HYDROXY-VITAMIN D₃ AND PROCESS FOR PREPARING SAME

[75] Inventors: Hector F. DeLuca; Yoko Tanaka, both of Madison, Wis.; Nobuo Ikekawa; Yoshiro Kobayashi, both of Tokyo, Japan

[73] Assignee: Wisconsin Alumni Research Foundation, Madison, Wis.

[*] Notice: The portion of the term of this patent subsequent to Feb. 19, 2002 has been disclaimed.

[21] Appl. No.: 639,776

[22] Filed: Aug. 13, 1984

Related U.S. Application Data

[63] Continuation-in-part of Ser. No. 524,269, Aug. 18, 1983.

[51] Int. Cl.⁴ ................................................ C07J 9/00
[52] U.S. Cl. ........................ 260/397.2; 260/239.55 R; 260/397.1
[58] Field of Search ..................................... 260/397.2

[56] References Cited

U.S. PATENT DOCUMENTS 4,196,133  4/1980  DeLuca et al. ................... 260/397.2
4,226,788 10/1980  DeLuca et al. ................... 260/397.2
4,397,847  8/1983  Boris et al. ............................ 424/236

OTHER PUBLICATIONS

Partridge et al., "Helvetica Chemica Acta.", vol. 57, Fasc 3 (1974), pp. 764–771.

*Primary Examiner*—Elbert L. Roberts
*Attorney, Agent, or Firm*—Howard W. Bremer

[57] ABSTRACT

The invention provides new derivatives of vitamin D, 23,23-difluoro-25-hydroxycholeacalciferol and the acylates thereof, a method for preparing said compounds and various new intermediates utilized in such process.

The derivative compounds are characterized by vitamin D-like activity as evidenced by their ability to increase intestinal calcium transport and serum calcium. The compounds are further characterized by resistance to hydroxylation at C-23, which is recognized as an essential metabolic step to the inactivation of vitamin D. The compounds should, therefore, provide vitamin D-like activity of greater time duration.

3 Claims, No Drawings

23,23-DIFLUORO-25-HYDROXY-VITAMIN D$_3$ AND PROCESS FOR PREPARING SAME

The invention described herein was made in the course of work under a grant or award from the Department of Health and Human Services.

The Government also has rights in this invention pursuant to U.S. Japan Cooperative Grant INT-76-05793 awarded by the National Science Foundation.

This application is a continuation-in-part of application Ser. No. 524,269, filed Aug. 18, 1983.

TECHNICAL FIELD

This invention relates to a compound which is characterized by vitamin D-like activity.

More specifically this invention relates to a derivative of vitamin D$_3$.

Vitamin D$_3$ is a well-known agent for the control of calcium and phosphorous homeostasis. In the normal animal or human this compound is known to stimulate intestinal calcium transport and bone-calcium mobilization and is effective in preventing rickets.

It is also now well known that to be effective, vitamin D$_3$ must be converted in vivo to its hydroxylated forms. For example, the vitamin is first hydroxylated in the liver to form 25-hydroxy-vitamin D$_3$ and is further hydroxylated in the kidney to produce 1α,25-dihydroxy vitamin D$_3$ or 24,25-dihydroxy vitamin D$_3$. The 1-hydroxylated form of the vitamin is generally considered to be the physiologically active or hormonal form of the vitamin and to be responsible for what are termed the vitamin D-like activities, such as increasing intestinal absorption of calcium and phosphate, mobilizing bone mineral, and causing reabsorption of calcium in the kidneys.

BACKGROUND ART

Since the discovery of biologically active metabolites of vitamin D there has been much interest in the preparation of structural analogs of these metabolites, because such compounds may represent useful therapeutic agents for the treatment of diseases resulting from calcium metabolism disorders. A variety of vitamin D-like compounds have been synthesized. See, for example, U.S. Pat. Nos. 3,741,996 directed to 1α-hydroxycholecalciferol; 3,907,843 directed to 1α-hydroxyergocalciferol; 3,786,062 directed to 22-dehydro-25-hydroxycholecalciferol; 4,069,321 directed to the preparation of various side chain-fluorinated vitamin D$_3$ derivatives and side chain-fluorinated dihydrotachysterol analogs; 4,201,881 directed to 24,24-difluoro-1α,25-dihydroxycholecalciferol and 4,196,133 directed to 24,24-difluoro-25-hydroxycholecalciferol. Other metabolic alternatives are believed to be responsible for the metabolism and ultimate elimination of vitamin D compounds from the body, with the generally accepted recognition that 1α,25-dihydroxycholecalciferol (U.S. Pat. No. 3,697,559) is the circulating hormonal form of vitamin D.

DISCLOSURE OF INVENTION

A new derivative of vitamin D has now been found which is at least as potent as 25-hydroxyvitamin D$_3$ (see U.S. Pat. No. 3,565,924) as measured by its ability to stimulate calcium transport in the intestine or its ability to mobilize calcium from bone. This derivative has been identified as 23,23-difluoro-25-hydroxycholecalciferol (23,23-difluoro-25-hydroxy vitamin D$_3$ or 23,23-F$_2$-25OH D$_3$.)

A major pathway for inactivation of vitamin D is 23S-hydroxylation of 25-hydroxy vitamin D$_3$ (Tanaka et al, Biochemistry 20, 3875–3879, 1981) and its subsequent conversion to 25R-hydroxy-26,23S-lactone (Tanaka et al, Proc. Nat'l. Acad. Sci. USA 78, 4805–4808, 1981). In view of these findings of Tanaka et al it would appear that the vitamin D derivative of the present invention, because of the fluorine substituents at C-23, would not be readily hydroxylated at that carbon and that, therefore, it would be characterized by prolonged vitamin D-like activity—a characteristic which would be an obvious advantage in many therapeutic applications.

BEST MODE FOR CARRYING OUT THE INVENTION 23,23-difluoro-25-hydroxyvitamin D$_3$ can be prepared in accordance with the process as hereinafter described and shown in the following schematic. In the schematic and the description like numbers identify like compounds. Also, for those compounds in the schematic where a particular steroid nucleus is not specifically depicted the designated compound has the same steroid nucleus shown for the compound from which it is not immediately derived. For example, compounds 2 and 3 have the steroid nucleus shown in compound 1, while compounds 5 through 14 have the steroid nucleus shown in compound 4.

The process comprises the following sequence of steps:

The steroid i ether (1) is oxidized to the C-22 aldehyde by pyridium chlorochromate or other suitable alcohol oxidizing reagent. This C-22 aldehyde is converted to a silyl ether carboxy ester (3) by a Wittig type condensation. Hydrolysis in acetic acid and TsOH afford the corresponding C-23α keto methyl ester and converts the i ether to the 3 acetoxy function (4). The ketone is fluorinated with DAST (diethyl amino sulfur trifluoride) to provide the C-23 difluoro carboxymethyl-3 acetate. Hydrolysis of the acetoxy group and treatment with 2,3 dihydropyan and TsOH gave the 3-THP protected difluoro 24 ester. Reduction with Li aluminum hydride produced the C-24 alcohol (7). Treatment of this alcohol with a mixture of trifluoromethanesulfonic anhydride and pyridine provides the trifluoromethanesulfonyl ester which undergoes a malonic ester condensation to yield the C-26,27 diethyl ester (9). N chloro succinimide is used to convert (9) to the C-25 chloro derivative (10) which, upon reduction with lithium aluminum hydride, affords the C-26,27 chlorodialcohol (11). Treatment of that chlorodiol with sodium hydride in dimethoxyethane yields the 25,26 expoxy 26-alcohol (12). Treatment with methanesulfonyl chloride and triethylamine provided the mesylate that upon reduction with lithium aluminum hydride yielded 23,23-difluoro,25-hydroxyl-3β tetrahydropyranyl cholesterol (13) that was converted to the acetate (14). This compound was then converted to the 5,7-diene using the usual allylic bromination followed by dehydrobromination in collidine. This dien was then photolyzed to provide the corresponding previtamin which during the temperatures of work up result in the 23,23-difluoro-25-hydroxyvitamin D$_3$ (16).

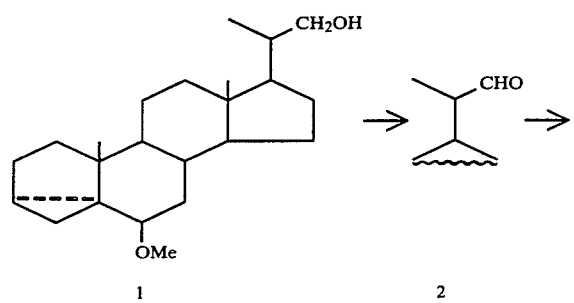
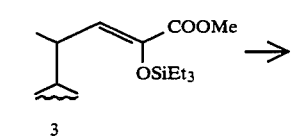
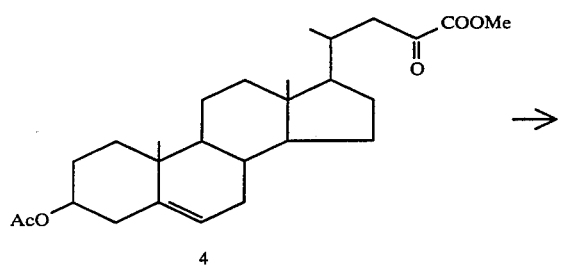
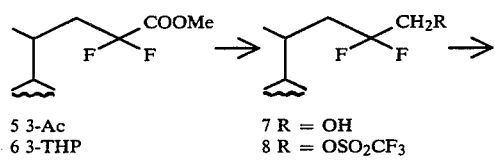

5 3-Ac
6 3-THP

7 R = OH
8 R = OSO₂CF₃

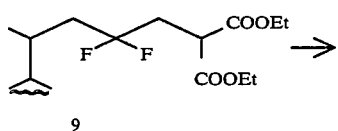

9

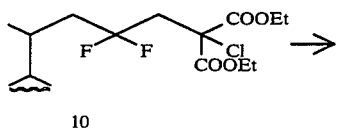

10

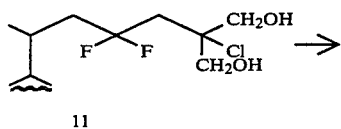

11

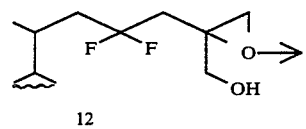

12

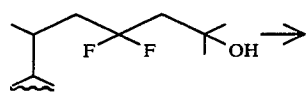

13 3-THP
14 3-Ac

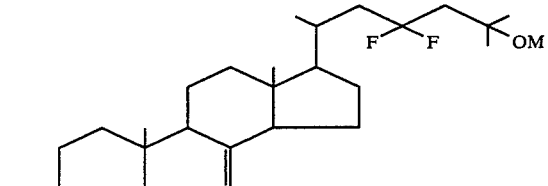

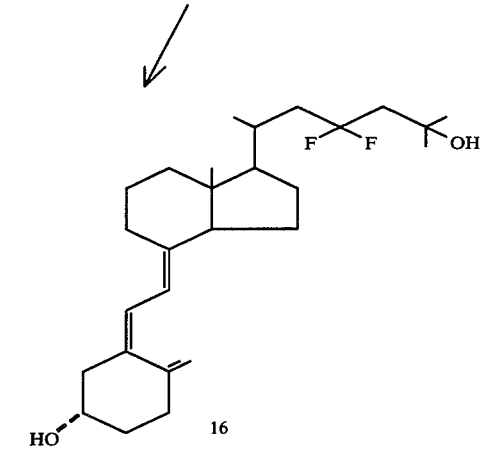

In the following detailed description of the synthesis of 23,23-difluoro-25-hydroxyvitamin $D_3$ the various physiochemical characteristics of the compounds shown were determined utilizing the apparatus hereafter described and the various abbreviations and processes have the indicated definitions.

Melting points were determined on a hot stage microscope and were uncorrected. UV spectra were obtained in ethanol solution with a Shimadzu UV-200 double beam spectrophotometer. IR spectra were taken with a JEOL IRA-1 diffraction grating infrared spectrophotometer. $^1$H-NMR spectra were recorded on a Varian EM-360L spectrometer in CDCl₃ unless otherwise stated, with tetramethylsilane as an internal reference. $^{19}$F-NMR spectra were recorded on a Varian EM-360L spectrometer in CDCl₃ solution, with benzotrifluoride as an internal reference (a plus means high field). Mass spectra were obtained with a HITACHI double focusing mass spectrometer RMU-7L. Column chromatography was effected with silica gel (Merck, 70-23 meah). Preparative thin layer chromatography was carried out on precoated plates of silica gel (Merck, silica gel 60 F₂₅₄). The usual work-up refers to dilution with water, extraction with an organic solvent, washing to neutrality, drying over magnesium sulfate, filtration, and removal of the solvent under reduced pressure. The following abbreviations were used; THF, tetrahydrofuran; ether, diethyl ether; HMPA, hexamethylphosphoramide; TsOH, p-toluenesulfonic acid; THP, tetrahydropyranyl; s, singlet; d, doublet; t, triplet; q, quartet; m, multiplet; bs, broaden singlet.

SYNTHESIS

6β-Methoxy-3α,5-cyclo-23,24-dinor-5α-cholan-22-al (2)

6β-Methoxy-3α,5-cyclo-23,24-dinor-5α-cholan-22ol (1) (2.0 g, 15.8 mmol), which was prepared according to the literature method (See Helvetica Chimica Acta Vol. 57, Fasc. 3 (1974) nr. 84–85 pp. 764–771), was added to suspension of pyridinium chlorochromate (3.8 g) and sodium acetate (1.4 g) in dichloro-methane (40 ml), and this mixture was stirred at room temperature for 2.5 hr. Then, to this solution ether (100 ml) was added and the resultant precipitates were filtered off and washed with ether (100 ml). The combined filtrate was successively washed with 5%NaHCO$_3$ and brine, and dried over magnesium sulfate. After removal of the solvent in vacuo, the residue was applied to a column of silica gel (300 g).

Elution with n-hexane-ether (10:1) provided the aldehyde (2) (1.44 g, 73%), amorphous. $^1$H-NMR δ: 0.76 (3H, s, 18-H$_3$), 1.30 (3H, d, J=6 Hz, 21-H$_3$), 1.17 (3H, s, 19-H$_3$), 2.76 (1H, m, 6-H), 3.33 (3H, s, —OCH$_3$), 9.51 (1H, d, J=3.5 Hz, —CHO). MS m/z: 344 (M+), 329, 312.

6β-Methoxy-23-triethylsilyloxy-3α,5-cyclo-5α-cholan-22-en-24-oic Acid Methyl Ester (3)

To a solution of diisopropylamine (1.05 ml, 7.5 mmol) in THF (10 ml) n-butyllithium (6 mmol) was added at −78° C. under argon atmosphere and this solution was stirred for 5 min. To this solution methyl α-triethylsilyloxy-α-dimethylphosphonoacetate (1.56 g, 5 mmol) in THF (10 ml) was added and this mixture was stirred at room temperature for 15 min. Then, to the resulting solution the aldehyde (2) (491 mg, 1.43 mmol) in THF (10 ml) was added and this mixture was stirred at room temperature for 4 hr. The usual work-up (ether for extraction) gave a crude product, which was applied to a column of silica gel (150 g). Elution with n-hexane-ether (15:1) provided the unsaturated ester (3) (615 mg, 81%), colorless oil. $^1$H-NMR δ: 3.30 (3H, s, —OCH$_3$), 3.73 (3H, s, —CO$_2$CH$_3$), 5.26 (1H, d, J=10 Hz, 22-H). MS m/z: 530 (M+), 501, 469.

3β-Acetoxy-23-oxochol-5-en-24-oic Acid Methyl Ester (4)

A solution of the unsaturated ester (3) (1.53 g, 2.9 mmol) in acetic acid (7 ml) was heated at 80°–90° C. for 6 hr. The usual work-up (ether for extraction) gave a crude product. This and a catalytic amount of TsOH in dioxane (10 ml) and water (10 ml) were heated at 85°–95° C. for 7 hr. The usual work-up (ether for extraction) gave a crude product, which was applied to a column of silica gel (300 g). Elution with n-hexane-ether (15:1) provided the α-keto ester (4) (768 mg, 76%), mp 146°–147° C. (n-hexane). IR $\gamma_{max}^{KBr}$ cm$^{-1}$: 1720, 1240. $^1$H-NMR δ: 0.73 (3H, s, 18-H$_3$), 0.93 (3H, d, J=6 Hz, 21-H$_3$), 1.03 (3H, s, 19-H$_3$), 2.03 (3H, s, acetyl), 3.88 (3H, s, —CO$_2$CH$_3$), 4.63 (1H, m, 3-H), 5.41 (1H, m, 6-H). MS m/z: 384 (M+—CH$_3$COOH), 369.

Anal. Calcd for C$_{27}$H$_{40}$O$_5$: C, 72.92; H, 9.08. Found: C, 72.63; H, 9.13.

3β-Acetoxy-23,23-difluorochol-5-en-24-oic Acid Methyl Ester (5)

A mixture of α-ketoester (4) (400 mg, 0.9 mmol) and diethylaminosulfurtrifluoride (1.5 ml, 9.5 mmol) in dichloromethane (15 ml) was stirred at room temperature for 16 hr. The usual work-up (ether for extraction) gave a crude product, which was applied to a column of silica gel (100 g). Elution with n-hexane-ether (10:1) provided the difluoroester (5) (312 mg, 74%), mp 132°–132.5° C. (n-hexane). IR $\gamma_{max}^{KBr}$ cm$^{-1}$: 1770, 1730, 1255. $^1$H-NMR δ: 0.70 (3H, s, 18-H$_3$), 1.0. (3H, s, 19-H$_3$), 1.10 (3H, d, J=6 Hz, 21-H$_3$), 2.03 (3H, s, acetyl), 3.87 (3H, s, —CO$_2$CH$_3$), 4.60 (1H, m, 3-H), 5.38 (1H, m, 6-H). $^{19}$F-NMR: +40.3. MS m/z: 406 (M+ —CH$_3$COOH). Anal. Calcd for CH$_{27}$H$_{40}$O$_4$F$_2$: C, 69.50; H, 8.64; F, 8.14. Found: C, 69.75; H, 8.75; F, 8.26.

23,23-Difluoro-3β-tetrahydropyranyloxychol-5-en-24-oic Acid Methyl Ester (6)

The difluoroester (5) (880 mg, 1.9 mmol) was treated with 2% KOH—MeOH (30 ml) at room temperature for 2 hr. The usual work-up (ether for extraction) gave a crude acid. This in ether (10 ml) was treated with etheral solution of diazomethane until the gas evolution was ceased. This solution was concentrated under reduced pressure to leave the residue. This is dioxane (10 ml) was treated with 2,3-dihydropyran (516 μl) and TsOH (10 mg) at room temperature for 3 hr. The usual work-up (ether for extraction) gave a crude product, which was applied to a column of silica gel (200 g). Elution with n-hexane-ether (15:1) provided the THP-ester (6) (907 mg, 95%), amorphous. $^1$H-NMR δ: 0.70 (3H, s, 18-H$_3$), 1.03 (3H, s, 19-H$_3$), 1.10 (3H, d, J=6 Hz, 21-H$_3$), 3.53 (2H, m, THP), 3.86 (3H, s, —CO$_2$CH$_3$), 3.93 (1H, m, 3-H), 4.73 (1H, m, THP), 5.36 (1H, m, 6-H). $^{19}$F-NMR δ: +40.0. MS m/z: 424 (M+-DHP), 406, 391.

23,23-Difluorochol-5-ene-3β,24-diol 3-THP Ether (7)

To a suspension of lithium aluminium hydride (63 mg, 1.65 mmol) in ether (10 ml) the difluoroester (6) (1.40 g, 2.76 mmol) in ether (10 ml) was added and the mixture was stirred at 0° C. for 10 min and then stirred at room temperature for 10 min. The usual work-up (ether for extraction) gave a crude product, which was applied to a column of silica gel (100 g). Elution with n-hexane-ether (5:1) gave the alcohol (7) (1.13 g, 86%), viscous oil. $^1$H-NMR δ: 0.73 (3H, s, 18-H$_3$), 1.03 (3H, s, 19-H$_3$), 1.13 (3H, d, J=6 Hz, 21-H$_3$), 3.33–4.10 (5H, m, 24-H$_2$, 3-H, and THP), 4.76 (1H, m, THP), 5.38 (1H, m, 6-H). $^{19}$F-NMR δ: +43.3. MS m/z: 396 (M+ -DHP), 378.

23,23-Difluoro-24-trifluoromethanesulfonyloxychol-5-en-3β-ol 3-THP Ether (8)

The mixture of pyridine (124 μl) and trifluoromethanesulfonic anhydride (206 μl) in dichloromethane (5 ml) was stirred at −20° C. under argon atmosphere for 5 min. To this solution the alcohol (7) (400 mg, 1.02 mmol) in dichloromethane (10 ml) was added and the mixture was stirred at room temperature for 40 min. The usual work-up (dichloromethane for extraction) gave the triflate (8) (612 mg), which was used in the next step without further purification. $^1$H-NMR δ: 0.73 (3H, s, 18-H$_3$), 1.00 (3H, s, 19-H$_3$), 1.15 (3H, d, J=6 Hz, 21-H$_3$), 3.56 (2H, m, THP), 3.85 (1H, m, 3-H), 4.50 (2H, t, J=12 Hz, 24-H$_2$), 4.70 (1H, m, THP), 5.37 (1H, m, 6-H). $^{19}$F-NMR δ: +12.2 (3F), +41.3 (2F).

23,23-Difluoro-3β-tetrahydropyranyloxycholest-5-ene-26,27-dioic Acid Diethyl Ester (9)

A mixture potassium tert-butoxide (1.1 g, 9.6 mmol) and diethyl malonate (3.8 g, 24 mmol) in THF (25 ml) and HMPA (8 ml) was stirred at room temperature under argon atmosphere for 1 hr. To this solution the triflate (8) (1.47 g, 2.4 mmol) in THF (20 ml) was added and the mixture was stirred at room temperature for 26 hr. The usual work-up (ether for extraction) gave a crude product, which was applied to a column of silica gel (100 g). Elution with n-hexane-ether (5:1) provided the diester (9) (1.20 g, 81%), mp 79°–80° C. (ethanol). IR $\gamma_{max}^{KBr}$ cm$^{-1}$: 1750, 1740. $^1$H-NMR δ: 0.73 (3H, s, 18-H$_3$), 1.00 (3H, s, 19-H$_3$), 1.10 (3H, d, J=6 Hz, 21-H$_3$), 1.27 (6H, t, J=7 Hz, —CO$_2$CH$_2$CH$_3$), 3.46 (2H, m, THP), 3.62 (1H, t, J=6 Hz, 25-H), 3.80 (1H,m, 3-H), 4.14 (4H,q,J=JHz, —COCH$_2$CH$_3$), 4.64 (1H,m,THP), 5.30 (1H m, 6-H). MS m/z: 538 (M$^+$-DHP), 520, 505. Anal. Calcd for C$_{36}$H$_{56}$O$_6$F$_2$: C, 69.40; H, 9.06; F, 6.10. Found: C, 69.19; H, 9.11; F, 5.85.

25-Chloro-23,23-difluoro-3β-tetrahydropyranyloxy-cholest-5-ene-26,27-dioic Acid Diethyl Ester (10)

The diester (9) (700 mg, 1.125 mmol) was treated with sodium hydride (39 mg, 1.625 mmol) in dimethoxyethane (20 ml) at room temperature under argon atmosphere for 1 hr. Then, to this solution N-chlorosuccinimide (180 mg, 1.35 mmol) was added and the mixture was stirred at room temperature for 1 hr. The usual work-up (ether for extraction) gave a crude product, which was applied to a column of silica gel (20 g). Elution with n-hexane-ether (10:1) provided tthe chlorodiester (10) (730 mg, 99%), glass. $^1$H-NMR: 0.72 (3H, s, 18-H$_3$), 1.02 (3H, s, 19-H$_3$), 1.10 (3H, d, J=6 Hz, 21-H$_3$), 1.30 (6H, t, J=7.5 Hz, —CO$_2$CH$_2$CH$_3$), 2.95 (2H, t, J=15 Hz, 24-H$_2$), 3.52 (2H, m, THP), 3.88 (1H, m, 3-H), 4.32 (4H, q, J=7.5 Hz, —CO$_2$CO$_2$CH$_3$), 4.72 (1H, m. THP), 5.38 (1H, m, 6-H). MS m/z: 554, 520.

25-Chloro-23,23-difluorocholest-5-ene-3β,26,27-triol 3-THP Ether (11)

To a solution of the chlorodiester (10) (730 mg, 1.1 mmol) in ether (15 ml) lithium aluminium hydride (48 mg) was added and the mixture was stirred at 0° C. for 1 hr. and then stirred at room temperature for 2 hr. The usual work-up (ether for extraction) gave a crude product, which was applied to a column of silica gel (50 g). Elution with dichloromethane provided the chlorodiol (11) (250 mg, 39%) mp 152°–153° C. (n-hexane-ether). $^1$-H-NMR δ(CDCl$_3$-acetone d$_6$-DMSO d$_6$): 0.77 (3H, s, 18-H$_3$), 1.00 (3H, s, 19-H$_3$), 1.10 (3H, d, J=6 Hz, 21-H$_3$), 3.50–4.50 (7H, m, 3-H, 26-H$_2$, 27-H$_2$, and THP), 4.77 (3H, m, 26-OH, 27-OH, and THP), 5.38 (1H, m, 6-H); δ(CDCl$_3$-acetone d$_6$-DMSOd$_6$-D$_2$O): 3.60 (2H, m, THP), 3.77 (4H, s, 26-H$_2$ and 27-H$_2$), 4.77 (1H, m, THP). MS m/z: 434, 416, 404. Anal. Calcd for C$_{32}$H$_{51}$O$_4$ClF$_2$: C, 67.05; H, 8.97; Cl, 6.19; F, 6.63. Found: C, 67.08; H, 8.89; Cl, 5.99; F, 6.53.

25ε)-25,26-Epoxy-23,23-difluorocholest-5-ene-3β,27-diol 3-THP Ether (12)

The chlorodiol (11) (183 mg, 0.32 mmol) was treated with sodium hydride (18 mg, 0.75 mmol) in dimethoxyethane (18 ml) at room temperature for 6 days. The usual work-up (ether for extraction) gave a crude product, which was applied to a column of silica gel (100 g). Elution with dichloromethane provided the epoxyalcohol (12) (56 mg, 32%), glass. $^1$H-NMr δ: 2.92 (2H, m, 26-H$_2$), 3.67–4.16 (3H, m, 3-H and 27-H$_2$). MS m/z: 434 (M$^+$-THP OH), 416, 404, and the recovery of chlorodiol 11 (92 mg, 50%).

23,23-Difluorocholest-5-ene-3β,25-diol 3-THP Ether (13)

The epoxyalcohol (12) (55 mg, 0.103 mmol) was treated with methanesulfonyl chloride (20 μl) and triethylamine (30 μl) in dichloromethane (10 ml) at room temperature for 13 hr. The usual work-up (ether for extraction) gave the crude mesylate (69 mg). This mesylate was treated with lithium aluminum hydride (5 mg) in ether (10 ml) at 0° C. for 1.5 hr. The usual work-up (ether for extraction) gave a crude product, which was applied to a column of silica gel (20 g). Elution with n-hexane-ether (5:2) provided the 25-ol (13) (43.3 mg, 80%), mp 148°–149° C. (n-hexane-cyclohexane). $^1$H-NMR δ: 0.72 (3H, s, 18-H$_3$), 1.01 (3H; s,19-H$_3$, 1.10(3H,d,J=6 Hz,21-H), 1.35 (6H,s,26-H$_3$ and 27-H$_3$), 3.53 (2H, m, THP), 3.87 (1H, m, 3-H), 4.71 (1H, m, THP), 5.37 (1H, m, 6-H). MS m/z: 420 (M$^+$-TEPOH), 405. High resolution MS Calcd for C$_{27}$H$_{42}$F$_2$O (M$^+$-THPOH): 420, 3214. Found: 420, 3208.

23,23-Difluorocholest-5-ene-3β,25-diol 3-Acetate (14)

The THP-ether (13) (26 mg, 0.0498 mmol) in methanol (4 ml) and THP (9) (4 ml) was treated with a catalytic amount of TsOH at room temperature for 1 hr. The usual work-up (ethyl acetate for extraction) gave the crude diol (21.4 mg). This diol was treated with acetic anhydride (1 ml) and pyridine (1 ml) at room temperature for 14 hr. The usual work-up (ethyl acetate for extraction) gave a crude product, which was applied to a column of silica gel (5 g). Elution with benzene-ethyl acetate (10:1) provided the acetate (14) (23.0 mg, 96%); mp 168°–170° C. (methanol). $^1$H-NMR δ: 0.82 (3H, s, 18-H$_3$), 1.02 (3H, s, 19-H$_3$), 1.07 (3H, d, J=6 Hz, 21-H$_3$), 1.35 (6H, s, 26-H$_3$ and 27-H$_3$), 2.03 (3H, s, acetyl), 4.55 (1H, m, 3-H), 5.36 (1H, m, 6-H). High resolution MS Calcd for C$_{27}$H$_{42}$F$_2$O (M$^+$ —CH$_3$COOH): 420, 3202. Found: 420, 3206.

23,23-Difluorocholesta-5,7-diene-3,25-diol (15)

To a solution of the acetate (14) (19 mg, 0.0396 mmol) in carbontetrachloride (2 ml) N-bromosuccinimide (10 mg, 0.0571 mmol) was added and this mixture was refluxed under argon atmosphere for 20 min. After cooling to 0° C., the resulting precipitate was filtered off. The filtrate was concentrated below 40° C. to leave the residue. This residue in xylene (2 ml) was added dropwise to a refluxing solution of S-collidine (0.5) and xylene (1.5 ml) and refluxing was continued for 20 min. The usual work-up (ethyl acetate for extraction) gave the crude diene. This diene in acetone (10 ml) was treated with a catalytic amount of TsOH at room temperature under argon atmosphere in the dark for 14 hr. The usual work-up (ethyl acetate for extraction) gave the crude 5,7-diene acetate. This acetate in THF (5 ml) was treated with 5% KOH-MeOH (1.0 ml) at room temperature under argon atmosphere in the dark for 30 min. The usual work-up (ethyl acetate for extraction) gave a crude product, which was submitted to preparative TLC (benzene-ethyl acetate 2:1, developed twice). The band of Rf value 0.47 was scraped off and eluted with ethyl acetate. Removal of the solvent provided the 5,7-diene (15) (3.75 mg, 21.7%). UV λ$_{max}$ mm: 294, 282, 272.

23,23-Difluoro-25-hydroxyvitamin D$_3$ (16)

A solution of the 5,7-diene (15) (3.75 mg, 8.60 μmol) in benzene (90 ml) and ethanol (40 ml) was irradiated with a medium pressure mercury lamp through a Vycor filter with ice cooling under argon atmosphere for 2.5 min. Removal of the solvent under reduced pressure gave a crude product, which was submitted to preparative TLC (benzene-ethyl acetate 2:1, developed twice). The band of Rf value 0.59 was scraped off and eluted with ethyl acetate. Removal of the solvent provided the vitamin $D_3$ derivative (16) (0.96 mg, 25.6%). This was further purified by high performance liquid chromatography on a Zorbax SIL normal phase column (4.6 mm$\Phi \times$15 cm) at a flow rate of 2 ml/min with hexane-dichloromethane (1:2) as an eluent. The retention time of (16) was 7.4 min. UV $\lambda_{max}$ nm: 265, $\lambda_{min}$ nm: 228. $^1$H-NMR $\delta$: 0.58 (3H, s, 18-$H_3$), 1.07 (3H, d, J=6.1 Hz, 21-$H_3$) 1.34 (6H, s, 26-$H_3$ and 27-$H_3$), 3.95 (1H, m, 3-H), 4.81 (1H, bs, 19-H), 5.04 (1H, bs, 19-H), 6.03 (1H, d, J=10.7 Hz, 7-H), 6.23 (1H, d, J=10.7 Hz, 6-H). MS m/z: 436 (M+), 418, 403, 398, 380, 378, 300, 271, 265, 145, 118. High resolution MS calcd for $C_{27}H_{42}F_2O_2$: 436, 3150. Found: 436, 3155.

It will be apparent that in the foregoing other reactants may be utilized which will provide equivalent substituents at various places in the compounds depicted in the abreviated schematic. For example, in compound 4 the acetoxy shown in the 3-position in the molecule could readily be some other acyloxy group where the acyl group contains from about 1 to 4 carbon atoms. Also the ethyl ester shown in the 26 and 27 positions in compounds 9 and 10 can as readily be another alkyl ester where the alkyl group is a lower alkyl group containing from about 1 to about 4 carbon atoms.

The compound, 23,23-difluoro-25-hydroxyvitamin $D_3$, can be readily obtained in crystalline form by recrystallization from appropriate hydrocarbon solvents, or combinations of such solvents with alcoholic solvents, e.g. a combination of hexane and methanol, as is well known in the organic chemical art.

If desired the free vitamin of this invention can be readily converted to its acylated form with the compounds of this invention then being broadly represented by the formula

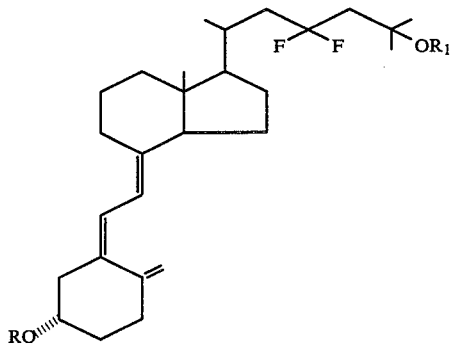

where

R and $R_1$ are each selected from the group consisting of hydrogen, an acyl group having from one to about four carbon atoms and benzoyl.

The conversion from the free vitamin to the acylate can be readily accomplished by reacting the free vitamin with the appropriate acyl chloride or anhydride, the acyl group of which will correspond to the acyl group which is desired to be present at either of the three or twenty-five position in the molecule, in pyridine at a temperature in the range from ambient temperature to reflux. For example, treatment of the free vitamin (1 mg) with acetic anhydride (0.1 ml) in pyridine (0.1 ml) at ambient temperature for 1.5 hours yields the corresponding 3-acetoxy derivative. The corresponding 3,25-diacetoxy derivative can be readily obtained by utilizing the same reagents at elevated temperatures, e.g. 75°–90° C. Similarly, the corresponding benzoate compound can be prepared by reaction of the free vitamin with benzoyl chloride in pyridine at room temperature for three hours.

Other acylates can also be prepared under like conditions with like reagents as will be readily evident to those skilled in the art.

BIOLOGICAL ACTIVITY

The biological activity of the new analog is evidenced by appropriate in vivo assays in the rat.

Male weanling rats (Holtzman Company, Madison, Wis.) were fed a low calcium vitamin D-deficient diet. (J. Nutr. 100, 1045–1052 (1970) for 3 weeks. They are then divided into three groups of 6 rats each. Rats in the control group were given 0.05 ml of 95% ethanol by intrajugular injection. Rats in the second group were administered, in same manner, a dose of 650 $p$mole of 25-hydroxyvitamin $D_3$ (25-OHD$_3$) dissolved in 0.05 ml ethanol, while rats in the third group were injected with a dose of 650 $p$mole of 23,23-difluoro-25-hydroxyvitamin $D_3$ (23,23-$F_2$-25-OHD$_3$) dissolved in 0.05 ml ethanol for comparative purposes. Twenty four hours after dosing, the effect of the test compounds on intestinal calcium transport and on bone calcium mobilization measured as by the serum calcium concentration were determined by the assay methods of Martin and DeLuca (Am. J. Physiol. 216, 1351–1359 (1969)) and of Tanaka et al (Biochemistry, 14, 3293–3296 (1975)) respectively. Results are shown in Table 1.

TABLE 1

| Compound given | Intestinal Calcium transport (Ca serosal/Ca mucosal) | Serum calcium (mg/100 ml) |
|---|---|---|
| Vehicle (ethanol) | 2.8 ± 0.4[a*] | 2.8 ± 0.1[d] |
| 25-OHD$_2$ | 5.5 ± 0.7[b] | 3.5 ± 0.05[e] |
| 23,23-$F_2$—25-OHD$_3$ | 5.0 ± 1.4[c] | 3.4 ± 0.2[f] |
| Significance of Difference: | [b] & [c] from [a] $p$ 0.005 [b] from [c] N.S. | [e] & [f] from [d] $p$ 0.001 [e] from [f] N.S. |

*Standard deviation of the mean

The foregoing data indicate that 23,23-$F_2$-25-OHD$_3$ is active in both intestine and bone and that the compound exhibits vitamin D-like activity at least as great as that exhibited by 25-hydroxyvitamin $D_3$, strongly suggesting its use as a substitute for that vitamin D derivative or for vitamin D.

The 23,23-difluoro-25-dihydroxycholecalciferol compound of this invention may be readily administered as sterile parenteral solutions by injection or intravenously or by alimentary canal in the form of oral dosages, or by suppository. Doses of from about 1 $\mu$g to about 25 $\mu$g per day are effective in obtaining the physiological calcium balance responses described and which are characteristic of vitamin D-like activity, with maintenance doses of about 5 $\mu$g being suitable.

Dosage form of the compounds can be prepared by combining them with a non-toxic pharmaceutically acceptable carrier as is well known in the art. Such carriers may be either solid or liquid such as, for example, corn starch, lactose, sucrose, peanut oil, olive oil, sesame oil and water. If a solid carrier is used the dosage forms of the compounds of the invention may be tablets, capsules, powders, troches or lozenges. If a liquid carrier is used, soft gelatin capsules, or syrup or liquid suspension, emulsions or solutions may be the dosage form. The dosage forms may also contain adjuvants, such as preserving, stabilizing, wetting or emulsifying agents, solution promoters, etc. They may also contain other therapeutically valuable substances.

It should be understood that although dosage ranges are given the particular dose to be administered to a host will depend upon the specific disease state being treated, the end results being sought in a particular case, as well as other factors known to those skilled in the art in the therapeutic use of such medicinal agents.

We claim:

1. Compounds having the formula

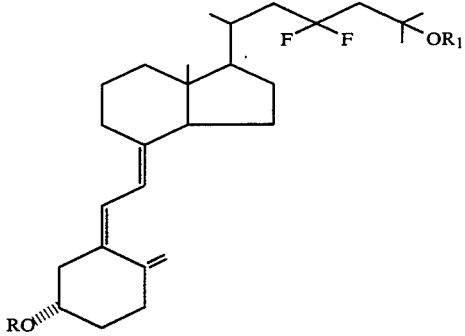

wherein R and $R_1$ are each selected from the group consisting of hydrogen, an acyl group having from one to about four carbon atoms and benzoyl, with the proviso that R and $R_1$ cannot both be hydrogen.

2. The compounds of claim 1 in crystalline form.

3. A compound having the formula

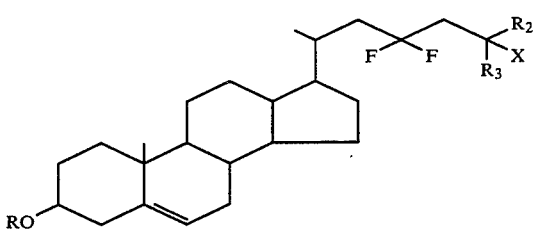

where $R_1$ is acetyl
X is hydroxy and
$R_2$ and $R_3$ are methyl.

* * * * *